United States Patent [19]

Wu et al.

[11] 4,069,017

[45] Jan. 17, 1978

[54] COLORIMETRIC ASSAY FOR BILIRUBIN

[75] Inventors: Tai-Wing Wu, Rochester; Glen Marshall Dappen, Webster, both of N.Y.

[73] Assignee: Eastman Kodak Company, Rochester, N.Y.

[21] Appl. No.: 759,529

[22] Filed: Jan. 14, 1977

[51] Int. Cl.$^2$ ............................................. G01N 33/16
[52] U.S. Cl. ............................... 23/230 B; 23/253 TP
[58] Field of Search ........................ 23/230 B, 253 TP

[56]  References Cited
U.S. PATENT DOCUMENTS

| | | | |
|---|---|---|---|
| 2,854,317 | 9/1958 | Free et al. | 23/230 B |
| 3,754,862 | 8/1973 | Wahlefeld et al. | 23/230 B |
| 3,814,586 | 6/1974 | Fraser, Jr. et al. | 23/230 B |
| 3,853,476 | 12/1974 | Rittersdorf et al. | 23/253 TP |
| 3,992,158 | 11/1976 | Przybylowicz et al. | 23/253 TP |

*Primary Examiner*—Robert M. Reese
*Attorney, Agent, or Firm*—Ronald P. Hilst

[57]  ABSTRACT

A colorimetric assay method for the detection of bilirubin in various liquid samples, particularly biological liquids. A multi-zone analytical element based on this assay method is also disclosed. The assay method employs an interactive mordant composition for bilirubin having one or more binding sites for bilirubin, such composition comprising a hydrophobic organic matrix and at least one charge-bearing cationic group. Upon mordanting of bilirubin by the interactive mordant composition, the mordanted bilirubin exhibits an absorption peak shift of at least 10 nm. and at least a 50% increase in molar extinction coefficient.

23 Claims, 3 Drawing Figures

COLORIMETRIC ASSAY FOR BILIRUBIN

FIELD OF THE INVENTION

The present invention relates to a colorimetric assay for the determination of bilirubin in various liquid samples such as biological liquids including body fluids such as blood serum, urine and the like. The assay of the invention is direct and highly sensitive and may be employed using either "wet chemistry", i.e., analytical chemical techniques sometimes referred to as solution assay techniques wherein chemical reagents are dissolved or suspended in a liquid vehicle, or "dry chemistry", i.e., analytical chemical techniques wherein chemical reagents are incorporated in various substantially "dry-to-the-touch" elements such as monolayer test strips, multilayer analytical test elements, and the like.

BACKGROUND OF THE INVENTION

Bilirubin is a degradation of hemoglobin. It has been estimated that each day approximately 6 to 7 grams of hemoglobin is released from damaged or aged red blood cells. From this pool of hemoglobin that is rapidly destroyed within the liver, spleen, and bone marrow, approximately 200–230 milligrams of bilirubin and its derivatives are formed each day in the normal human adult. Subsequently, as a part of normal human metabolic processes the major portion of this daily bilirubin production is excreted, degraded into other derivatives, etc.

In some cases, however, an excessive amount of bilirubin occurs within the human body through overproduction of bilirubin as in the case of excessive hemolysis or by retention of bilirubin due, for example, to a liver failure. Invariably, the result of an excessive amount of bilirubin within the human body is jaundice. This widely encompassing pathological condition is characterized by markedly elevated serum bilirubin levels, for example, 10 milligrams of bilirubin per deciliter of serum or higher compared to the normal adult range of 0.1 to about 1 milligram of bilirubin per deciliter of serum, and almost always there is also present a brownish-yellow pigmentation of the skin, sclera, or mucous membranes. In addition, there is increasing evidence suggesting that excess amounts of bilirubin in the blood can lead to an undesirable increase in bilirubin concentration within body cells and interfere with various cellular processes. For example, bilirubin has been widely implicated as a potent inhibitor of many enzymatic reactions that generate energy vital to the cell. Given this background, the clinical diagnostic significance of bilirubin, in tests for liver and other related organ functions, is self-evident.

The literature on bilirubin assay methodology is quite voluminous. Good reviews outlining many of the diverse bilirubin assay techniques can be found by reference to the text entitled *Clinical Chemistry-Principles and Technics*, edited by R. J. Henry, D. C. Cannon, and J. W. Winkelman, Harper and Row Publishers, 2nd Edition, pages 1042–1079 (1974). A further review of bilirubin assay techniques appears in *Fundamentals of Clinical Chemistry*, edited by N. W. Tietz, and published by W. B. Saunders Co. pages 743–762 (1970). Perhaps the most widely used analytical procedure for bilirubin assay work has been the so-called diazo method. The diazo method employs a coupling reaction of bilirubin with a diazonium salt, such as diazosulfanilic acid, to form a pigment having an extinction coefficient higher than bilirubin by itself (which has a yellow coloration). Typically, the diazo reaction procedure for bilirubin assay includes two kinetic phases: First, a so-called "direct reaction", in which color forms quite rapidly and then an "indirect reaction", in which color develops only after the addition of methanol. As outlined in the above-noted literature reviews, particularly that of Winkelman et. al., some confusion exists in the art with respect to what these two kinetic phases actually indicate. Some people consider the direct reaction a measure of unbound or free bilirubin while the indirect reaction is considered a measure of albumin-bound bilirubin. Others have thought the direct reaction measures conjugated bilirubin while the indirect method measures the unconjugated form of bilirubin.

In addition to the above-noted confusion existing with respect to the diazo method for bilirubin assay, Winkelman et al., in their critical review of the diazo method have concluded that in view of the many variants of the diazo procedure and the complexity of the diazo reaction itself, the analytical results obtained are often different. In addition, the diazo assay method, because of its requirement of using several different reagents which must be mixed shortly before the assay determination, generally requires a fairly long period of time and can be inaccurate because of other components in human serum and other biological fluids which will also respond to diazotization.

In addition to the above-noted diazo assay method and related variants thereof for determination of bilirubin, a number of other bilirubin assay techniques have been suggested or employed at one time or another. Among others, there are various direct, spectrophotometric (i.e., colorimetric) assay techniques for bilirubin which take advantage of the molar absorbtivity inherent in bilirubin. That is, free bilirubin is a yellow pigment having a molar absorbtivity of about $5 \times 10^4$ as measured at 435 nanometers. However, although the molar absorbitivity of bilirubin is high enough to be useful in various direct spectrophotometric solution techniques, it is not sufficiently high to produce a good quantitative assay of bilirubin using "dry chemistry" analytical test elements, for example, an analytical element of the type disclosed in Pryzbylowicz and Millikan, U.S. Pat. No. 3,992,158, issued Nov. 16, 1976. Thus, present-day direct spectrophotometric assay techniques for bilirubin are generally limited to solution assay techniques, particularly if accurate, quantitative results are desired. In addition, as noted in the above-referenced articles receiving various bilirubin assay techniques (see the Winkelman et al article noted above), direct spectrophotometric assay determinations for bilirubin suffer from spectral interferences due to the presence of hemoglobin which exhibits absorption peaks at 414, 540, and 576 nanometers. In addition, other materials present in bilirubin-containing biological fluids such as human serum can also cause spectral interferences using such direct spectrophotometric assay methods. For example, carotenoids can interfere with bilirubin assay because beta-carotene, one of the principal carotenoid components, exhibits an absorption peak at about 450 nm. which is in a region of the spectrum close to the absorption peak of bilirubin.

In addition to the above-noted spectral interferents for bilirubin using a direct spectrophotometric assay technique, it has been found that such techniques can also suffer interference due to the presence of other protein materials in human serum, such as albumin, to which bilirubin can bind and which as a result of such binding can cause a shift in the absorption intensity and absorption peak of bilirubin. As a result of the above-noted problems, among others, the art has had to rely substantially on the aforementioned diazo assay method for bilirubin determination or upon various modifications of the above-described direct spectrophotometric determination for bilirubin. For example, in U.S. Pat. No. 3,569,721 there is illustrated a direct spectrophotometric technique for determination of bilirubin wherein the spectral interference of hemoglobin is allegedly eliminated by, in essence, measuring the fluid sample to be tested at a wavelength for bilirubin maximum absorption and at a second wavelength for which hemoglobin, alone, is known to exhibit an absorption peak. One must then adjust the absorption peak for bilirubin concentration by an amount equivalent to the amount of hemoglobin determined to be present in the liquid sample.

Still another technique which has been used for the assay of bilirubin relates to the use of a reagent composition for bilirubin containing an organic acid or its salt such as trichloroacetic acid or an organic sulfonic acid, together with a ferric ion. In this method, bilirubin is oxidized by the organic acid or its salt in the presence of the ferric ion to a reaction product such as biliverdin and/or cholecyanin, which reaction product exhibits a characteristic blue or blue-green color and intensity which is related to the amount of bilirubin originally present. Such bilirubin assay techniques are described for example in U.S. Pat. No. 3,348,920 issued Oct. 24, 1967; U.S. Pat. No. 3,607,093 issued Sept. 21, 1971; and Belgium Pat. No. 816,927 filed Oct. 16, 1974. However, this method also suffers from many of the drawbacks noted above with respect to the diazo assay method and the direct spectrophotometric assay method. For example, the use of this assay method employing an organic acid or acid salt together with a ferric ion generally requires a substantial amount of time involving up to about 10 minutes for the reaction between the acid and bilirubin to go to completion and then an additional amount of time required to separate the final product from the original reaction media so that it may be analyzed spectrophotometrically. In addition, this test also is subject to various spectral interferents which exhibit absorption maxima in the blue region of a spectrum such as hemoglobin, various carotenoids, and the like.

SUMMARY OF THE INVENTION

In accord with the present invention there is provided a direct, colorimetric method for the determination of bilirubin in an aqueous liquid test sample which comprises contacting together the liquid test sample and an interactive mordant composition for bilirubin having one or more binding sites for bilirubin. The interactive mordant composition comprises a hydrophobic matrix and at least one charge-bearing cationic group. As a result of interaction between bilirubin contained in the liquid test sample and the above-described interactive mordant composition, bilirubin is mordanted, i.e., binds to the interactive mordant composition, and there is produced a shift of at least about 10 nm. in the absorption peak of bilirubin and at least a 50 percent increase in the molar extinction coefficient of bilirubin (as measured at the new absorption peak). Preferably, in accord with certain especially useful embodiments of the invention, the absorption peak of the mordanted bilirubin is shifted to a wavelength of 460 nm. or greater and the molar extinction coefficient of the mordanted bilirubin is increased to a value of $7.5 \times 10^4$ or greater.

The method of the present invention is useful for analysis of bilirubin in biological liquids such as blood, blood serum, urine, etc., particularly blood serum, because it minimizes the effect of many common bilirubin interferents such as hemoglobin, carotenoids, and others. This is achieved, in part, by the significant increase in molar extinction coefficient of the mordanted bilirubin and, in part, by the shift in the absorption peak of the mordanted bilirubin, both of these spectral changes occurring as a result of the bilirubin binding to the interactive mordant composition used in the invention. Of course, when using the assay of the invention to analyze the bilirubin content of various biological liquids, it may still be desirable to remove and dissociate (from bilirubin) various higher molecular weight protein interferents to which bilirubin can bind, for example, albumin, so that one can obtain a quantitative analysis for total bilirubin contained in the test liquid. For this reason, in accord with one embodiment of the invention, the test liquid can be subjected to a preliminary treatment for separation or removal of such bilirubin interferents. Such preliminary treatment can comprise conventional techniques adapted for the removal of high molecular weight protein interferents for bilirubin, such as protein precipitation, sample dilution, and the like.

Alternatively, in accord with an especially preferred embodiment, the bilirubin assay described above is carried out by use of an analytical element of the invention for the detection of bilirubin in a liquid. Such an element comprises a reagent zone, for example, a layer comprising the above-defined interactive mordant composition for bilirubin, and a spreading zone or layer which can distribute or meter the liquid test sample to the reagent zone. If desired, a surfactant can be incorporated into the spreading zone in an amount effective to normalize transport of bilirubin through this zone, even in the presence of widely varying amounts of high molecular weight protein interferents for bilirubin such as albumin and the like. If the particular liquid sample to be analyzed is first subjected to an independent preliminary treatment step for removal of substantially all protein interferents for bilirubin (e.g., protein precipitation or sample dilution), one can design an element for assay of bilirubin in accord with the present invention based solely upon the use of an element containing the above-defined reagent zone.

In accord with a further aspect of the invention, the reagent zone of the above-described analytical elements for the assay of bilirubin is preferably impermeable to higher molecular weight protein interferents for bilirubin, e.g., albumin and other proteins which have molecular weights of about 60,000 or greater, to further alleviate interference from such materials.

In accord with a further embodiment, the elements of the invention are integral elements wherein the spreading zone and reagent zone are superposed layers carried on a suitable support, such as a "radiation transmissive" support. As used herein, the term "radiation-transmissive" describes zones, supports and other layers of an analytical element that permit effective passage of electromagnetic radiation used to detect an analytical result produced in the element. Such transmissiveness includes transmission of electromagnetic radiation of a wavelength or wavelengths within the region between about 300 nm. and 700 nm. In accord with this embodiment of the invention, separate interlayers may be incorporated between the reagent layer and the support or between the spreading layer and the reagent layer, if desired. Such interlayers can contain additional reagents to, for example, remove various possible interferents from an aqueous liquid sample being analyzed or, if desired, such interlayers can contain hydrophilic, water swellable materials, e.g., gelatin, to enhance transport of the liquid sample through a multilayer test element of the invention.

In accord with the invention, the various individual layers or zones of the analytical elements described herein are, at least under conditions of use, in fluid contact with one another. Such fluid contact has reference to the ability of a liquid to pass between superposed or abutting layers or zones of an analytical element. Stated in another manner, fluid contact refers to the ability of components of a liquid to pass between the layers or zones in fluid contact. Although layers or zones in fluid contact can be contiguous, they may also be separated by intervening layers or zones. However, layers or zones in the element that physically intervene layers or zones in mutual fluid contact will also be in fluid contact therewith and will not prevent the passage of fluid between such layers or zones.

Fluid contact between layers or zones can be achieved by preparing elements having layers or zones that are initially contiguous or effectively so for purposes of fluid passage. Alternatively, it may be appropriate to prepare elements that have layers or zones initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers or zones, it may be necessary to apply compressive force or otherwise provide means to bring layers or zones of the element into fluid contact at the time of its use to provide an analytical result.

As used in the specification and claims herein, the term "permeable" denotes the ability of a substance, layer, or zone to be penetrated effectively by a material carried, i.e., distributed in as by dissolution or dispersion, in a liquid.

In operation, a preferred analytical element of this invention can receive a liquid sample which, if bilirubin positive, interacts with the interactive mordant composition within the reagent layer to provide a shift of at least about 10 nm. in the absorption peak of free bilirubin and an increase in the molar extinction coefficient of free bilirubin (as measured at the shifted absorption peak) to a value in excess of about $7.5 \times 10^4$. Free bilirubin, as used in the present disclosure, is defined to include conjugated or unconjugated bilirubin which is not bound to serum protein. Free bilirubin typically exhibits an absorption peak at a wavelength in the range of from about 435 to about 440 nm. and a molar absorptivity ($E_m$) of about $5 \times 10^4$ as measured in aqueous solution at 22° C. and at a pH of about 7.4 Unless otherwise stated, all molar absorptivity values noted herein are measured in aqueous medium at approximately 22° C and at a pH of about 7.4.

If a spreading layer is included in an element, an applied sample will usually pass through this layer prior to entering the reagent layer, and bilirubin will be distributed within the spreading layer to provide a uniform apparent concentration of such material at the surface of the spreading layer facing the reagent layer. It is possible to obtain such uniform apparent concentration over a wide range of sample volumes applied to the element. Due to fluid contact between the spreading layer and the reagent layer and also to the preferred uniform permeability of the reagent layer to bilirubin spread within the spreading layer, uniformly metered constituents are provided from the spreading layer to the reagent layer and can penetrate the reagent layer essentially without the occurrence therein, at any instant in time, of significant variations in the apparent concentration of bilirubin. Due to the presence of the interactive mordant composition in the reagent layer, and a uniform apparent concentration of bilirubin provided from the spreading layer to the reagent layer, a uniform quantitative detectable change can be produced in the element. Such a change can be detected quantitatively by radiometric techniques and, if desired, by automatic radiometric sensing devices such as photometric devices.

Preferably, the bilirubin assay method of the present invention is carried out by employing analytical elements, as described above, which employ "dry chemistry" and contain a spreading zone. This is because these analytical elements have surprisingly been found to effectively eliminate most common interferents for bilirubin analysis. Not only can these elements eliminate interference from carotenoids and hemoglobin, but in addition these elements show little or no interference to sodium chloride or total proteins contained in a given liquid test sample.

However, it will be appreciated that the method of the present invention can also be conveniently carried out using various "wet chemistry" or solution assay techniques. In such case, the interactive mordant composition for bilirubin incorporated in a suitable liquid medium is contacted with a liquid sample containing bilirubin. When using a "wet chemistry" or solution assay, it is preferred to subject the bilirubin-containing liquid test sample to a preliminary treatment step for eliminating high molecular weight protein interferents for bilirubin. This can be conveniently carried out using any of the above-noted separation techniques.

Prior to the present invention, various multilayer integral analytical elements containing a mordant and having a structural configuration somewhat similar to certain of the analytical elements described herein have been prepared or proposed. Such analytical elements are described in Clement, U.S. Ser. No. 691,265, filed June 25, 1976; Goffe et. al., U.S. Ser. No. 680,619, filed Apr. 26, 1976; Figueras, U.S. Ser. No. 759,527, entiled "Element for Analysis of Liquids", filed concurrently with the present application; and Wu, U.S. Ser. No. 759,530, entitled "Assay for Bilirubin", filed concurrently with the present application. With the exception of the aforementioned Wu patent application, none of the above-noted patent applications describe an element which contains a specific reagent material intended to test for or detect bilirubin. In addition, the mordants in each of the analytical elements described in each of the foregoing patent applications were incorporated therein to mordant a material other than the analyte of choice which those elements were designed to detect, e.g., a highly colored visible dyestuff or a fluorescent probe, the material so mordanted having been generated or released internally from a reagent zone or layer within the element as a result of interaction of the analyte of choice or a reaction product of the analyte generated within the element. In contrast, the integral analytical elements described in the present application contain in the reagent zone or reagent layer thereof an interactive mordant composition specifically incorporated therein to detect for bilirubin; and these integral elements are free from any reagent zone or layer which contains a highly colored dyestuff or fluorescent probe material or a precursor for such materials which interacts with an analyte contained in a liquid test sample applied to the element or an analyte reaction product generated within the integral element.

BRIEF DESCRIPTION OF THE DRAWING

In the accompanying drawings, each of
FIG. 1

DESCRIPTION OF THE PREFERRED EMBODIMENT

As indicated hereinabove, an essential feature of the present invention is the use of an interactive mordant composition for bilirubin having one or more binding sites for bilirubin. The mordant composition comprises a hydrophobic organic matrix and at least one charge-bearing cationic group. In accord with the present invention, it has been found that materials having the above-defined properties and composition bind bilirubin and therefore a material having these properties, functions as a mordant for bilirubin. However, not only do such materials act as mordants for bilirubin, but, in addition, it has been found that, upon interaction of bilirubin with such compositions, bilirubin is mordanted by the binding sites of the interactive composition and there is produced in the mordanted bilirubin a significant change in spectral characteristics as compared to free bilirubin. In particular, there is a marked shift in the absorption peak exhibited by the mordanted bilirubin as compared to that of free bilirubin, and there is a substantial increase in the molar extinction coefficient exhibited by the mordanted bilirubin as compared to free bilirubin.

In accord with certain preferred embodiments of the present invention, it has been found that polymeric mordants which have previously been used in various photographic films, papers and other applications, and which have a composition which contains repeating monomeric units containing charge-bearing cationic groups and which contains on the same or on other monomeric units thereof organo groups to impart hydrophobicity provide interactive mordant compositions for bilirubin which are especially effective. Of course, it should be recognized, that other polymeric materials having the above described properties and chemical composition, but which have not heretofore been identified as useful photographic mordants in the photographic arts can also be employed within the scope of the present invention.

Particularly useful polymeric interactive mordant compositions which can be employed in the invention include materials having in the polymer chain, monomeric units of formula I below:

I.

wherein
A represents an organo group and constitutes a portion of a polymer backbone,
Q represents a chemical bond(s) or a chemical group linking M+ to A;
M+ represents a cationic group, preferably a quaternary ammonium or phosphonium group, and
X− represents an acid anion such as a halide ion, for example, chloride or bromide; nitrate; methosulfate; p-toluenesulfonate; etc.

In accord with certain especially useful embodiments of the invention, M+ represents a quaternary ammonium or phosphonium group having Formulas II and III below:

II.

III.

wherein
each of $R^1$, $R^2$, and $R^3$, which may be the same or different, represent an aryl, an aralkyl, or an alkaryl group having from 5 to less than about 20 carbon atoms or an alkyl group having from 1 to about 10 carbon atoms.

Preferably, Q, in Formula I represents a hydrocarbon group preferably an arylene, arylenealkylene, alkylenearylene, arylenebisalkylene, or alkylenebisarylene group. Typically, although not required, Q contains from about 5 to about 10 carbon atoms.

As will be appreciated, A in Formula I above can vary depending upon the particular polymeric backbone selected for use. Especially good results, however, have been obtained when a represents an alkylene group. Typically, such alkylene groups contain from 2 to about 10 carbon atoms.

The polymeric interactive mordant compositions, which have been found useful in the present invention, can be homopolymers or copolymers, copolymers having been found particularly useful. A partial listing of representative such copolymers includes polymeric interactive mordant compositions containing recurring units having Formula I hereinabove, and, in addition, up to about 75 weight percent of additional recurring units comprising the residue of non-interfering monomers. The term "non-interfering repeating units" is used in the present invention to include chemical units which do not chemically or physically interfere with the above-described mordanting of bilirubin. Monomer precursors which provide such non-interfering repeating units and which also impart hydrophobicity to the resultant mordant polymer include aliphatic and aromatic hydrocarbons, such as olefins, substituted olefins, styrene, and substituted styrenes; alkyl acrylates and methacrylates and derivatives thereof; and known equivalents for such monomer precursors. In addition, if desired, polymeric interactive mordant compositions useful in the invention can be crosslinked so that individual polymeric chains are, for example, covalently crosslinked by difunctional crosslinking groups such as divinylbenzene, ethylene dimethacrylate, as well as a variety of other known equivalent such difunctional crosslinking groups. Typically, if such difunctional crosslinking groups are present, they are contained in a polymeric interactive mordant composition of the invention in the range of up to about 5 weight percent, preferably from about 0.1 to about 2 weight percent, based on the total weight of monomers present in the copolymerizable blend of monomers used to prepare such crosslinked polymer. Typically, representative copolymers useful as interactive mordant compositions in the present invention are copolymerized from a monomeric blend containing (a) from about 25 to about 90 weight percent of monomer precursors for repeating units having formula I above, (b) from about 10 to about 75 weight percent of monomer precursors for non-interfering repeating units and (c), if present, 0 to about 5 weight percent of a difunctional crosslinking agent.

Although certain preferred interactive mordant compositions used in the present invention have been described immediately hereinabove as polymeric materials, it will be appreciated that one can also use monomeric materials having the requisite hydrophobicity and cationic group to mordant bilirubin. When such monomeric mordant materials are employed in the present invention in an analytical element which employs "dry chemistry", it is preferred that such monomeric mordant compositions possess a molecular configuration or a sufficiently high molecular weight so that the material can be immobilized within the reagent zone of the element.

A partial listing of individual representative interactive polymeric mordant compositions for bilirubin in accord with the present invention includes the following materials:

Table I

| | Name | Structure |
|---|---|---|
| 1. | Poly(N,N,N-trimethyl-N-vinyl-benzylammonium chloride) |  |
| 2. | Poly[styrene-co-benzyl-(dimethyl)-p-vinyl-benzyl-ammonium chloride] |  |
| 3. | Poly(N,N,N-trioctyl-N-vinyl-benzylphosphonium chloride) |  |

Table I-continued

| Name | Structure |
|---|---|
| 4. Poly[styrene-co-(vinylbenzyl)-(trihexyl)-ammonium chloride] |  |
| 5. Poly(N,N,N-trimethyl-N-vinylbenzylammonium chloride-co-styrene) |  |
| 6. Poly(styrene-co-N-vinylbenzyl-N,N-dimethylbenzyl-ammonium chloride-co-divinylbenzene) |  |

The interactive mordant composition useful in the present invention can be prepared by well-known chemical reaction techniques which have been extensively described in connection with the use of these same or similar materials in the photographic arts. Accordingly, a detailed description for preparing various mordant materials used in the present invention is unnecessary. However, if specific details for the preparation of such materials is desired, reference can be made to the following patents: British Pat. No. 1,261,925; U.S. Pat. Nos. 3,488,706; 3,557,066; 3,625,694; 3,709,690; 3,770,439; 3,758,445; 3,773,509; 3,859,096; 3,898,088; 3,944,424; and 3,958,995.

The amount of the above-described interactive mordant composition for bilirubin which is required in the bilirubin assay of the invention can vary. Typically, in any given case, the amount of such interactive mordant composition will depend upon the particular range of bilirubin content i.e., the "dynamic range", over which a specific bilirubin assay is designed to be useful. In accord with various preferred embodiments of the invention wherein 1 mole of bilirubin is bound or mordanted to a material containing 1 molar equivalent amount of binding site for bilirubin, there should be sufficient interactive mordant composition so that there is at least one molar equivalent of binding site for bilirubin present in the interactive mordant composition for the maximum number of moles of bilirubin for which that element is intended. As will be appreciated, where the interactive mordant composition for bilirubin comprises a polymeric material, the amount of such polymeric material required will depend upon the average number of repeating units containing a binding site for bilirubin which are present in such polymeric mordant material and, as noted above, the dynamic range over which a specific bilirubin assay which employs such polymeric material is designed to be useful. In accord with a preferred embodiment of the present invention wherein a polymeric mordant material such as any one of polymeric mordants 1-6 listed above are employed and wherein such polymeric mordants are prepared from an intermediate copolymer of styrene and vinylbenzyl chloride having an inherent viscosity (as measured at 25° C in benzene at a concentration of 0.25 g/dl.) of about 0.15 to about 1.0, one typically employs an amount of such mordant composition within the range of from about 0.01 to about 1.0 g/dl. of mordant for a dynamic range of about 0.1 to 50 mg./dl. of bilirubin analyte. In general, it has been found useful to have present in the reagent zone of the assay elements of the invention, an excess amount of interactive mordant composition so that one can accelerate the interaction of bilirubin with the mordant materials to obtain the desired change in spectral properties of the mordanted bilirubin.

As noted earlier herein, the method of the invention may be carried out as a solution assay, or in accord with a preferred embodiment of the invention by use of "dry chemistry" employing, for example, an integral analytical element of the invention.

When the method of the invention is carried out as a solution assay, one carries out an analysis by first preparing in a suitable "wet" reaction zone, such as a radiation-transmissive container, an appropriate interactive mordant composition, as described above, dissolved or dispersed in a non-interfering liquid medium. Such non-interfering liquids include those liquid materials which, under conditions of use, do not substantially interfere with the interaction of bilirubin and mordant composition or with the absorption peak of free and mordanted bilirubin. Such non-interfering liquids include a variety of both aqueous and organic liquids. Typically, because of the application of the methods of the present invention to the analysis of biological fluids, it is advantageous to choose as the non-interfering liquid used in the reaction zone, an aqueous liquid such as water or various similar polar organic solvents, e.g., lower alkyl alkanols. If desired, depending upon the particular interactive composition, it may be useful to include various buffering materials in the reaction zone, in addition to the interactive composition.

In general, bilirubin assays carried out by "wet chemistry" techniques in accord with the present invention have been found to yield advantageous results when carried out using a buffered aqueous liquid having a pH range of from about 6.8 to about 9.5 and at a temperature within the range of from about 15° to about 60° C, preferably from about 22° to about 50° C. Of course, depending upon the particular interactive composition selected, one can vary the aforementioned pH and temperature of the reagent zone to values above or below the aforementioned ranges providing, of course, that one does not use a pH or temperature which causes undesired side reactions or significant degradation of bilirubin or interactive mordant composition. In addition, when the method of the invention is carried out as a solution assay, it is desirable to carry out the assay in the dark or under yellow safelight conditions to avoid light induced degradation of bilirubin.

When the method of the present invention is carried out as a "wet" assay for bilirubin, it is desirable, as explained hereinabove, to first preliminarily treat the bilirubin-containing liquid test sample to dissociate the bilirubin from various materials to which it may be bound. For example, where the liquid test sample is blood serum, it is known that a large amount of the bilirubin in the serum is bound to albumin also present in the serum. Various techniques have been devised in the art to dissociate bilirubin from materials such as albumin, and such methods may be employed as a preliminary treatment step in accord with the method of the present invention so that the resultant assay provides an accurate determination of total bilirubin contained in the serum sample. Such known methods for affecting dissociation between bilirubin and various serum protein, particularly albumin, include the use of various protein precipitation techniques, sample dilution techniques, and the like. A brief review of many of these different procedures may be found for example in the aforementioned Winkelman et. al. publication, i.e., *Clinical Chemistry-Principles and Technics,* Second Edition, 1974, pages 1042 through 1079.

Figure 1:
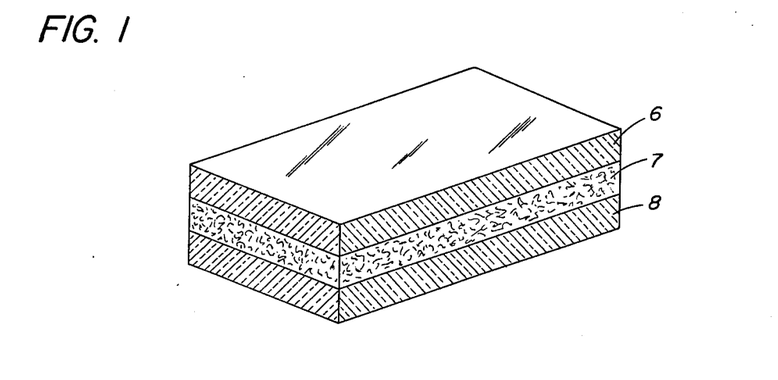
Figure 2:
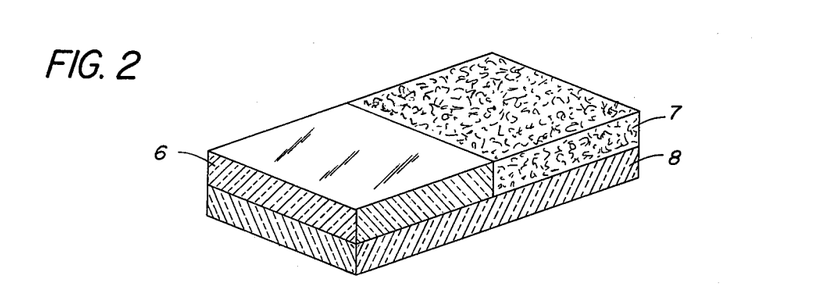
FIG. 2 is an enlarged sectional view of a preferred embodiment illustrating an analytical element of the invention

As noted hereinabove, the bilirubin assay method of the present invention is adaptable to both solution and the so-called "dry" chemical analysis techniques. Because of handling ease and other overall convenience features as well as the ability to provide quantitative analytical results, the use of the present invention in an analytical element as illustrated in FIGS. 1 and 2 for the "dry" analysis of bilirubin is especially preferred. Such an element, as illustrated in FIG. 1, comprises an essentially dry reagent zone 7 containing the above-described interactive mordant composition. An essentially dry spreading zone 6 and/or additional interlayers can also be present in the analytical element so that a preferred analytical element of the invention typically comprises at least two distinct zones which are in fluid contact with one another under conditions of use. Preferably, the various zones are present in an element of the invention as superposed, contiguous layers. Typically, these layers are coated on a support 8, preferably a radiation transmissive support. It will be appreciated, however, that although preferred analytical elements of the invention are composed of superposed, contiguous layers, other elements may also be prepared in accord with the invention having a different structural arrangement such as the use of an element as shown in FIG. 2 having two adjacent abutting zones, namely a spreading zone 6 and a reagent zone 7, carried on a support 8, if necessary or desired. For purposes of convenience and for illustrating the best mode of the invention, the elements of the present invention will hereinafter be described in terms of their structure and characteristics as observed in a multilayer, integral analytical element wherein the different zones are present as superposed, contiguous layers carried on a radiation transmissive support.

An integral element of the invention typically includes a spreading layer and a reagent layer, both of which are preferably radiation-transmissive. Such elements can have the layers on a support, preferably radiation-transmissive; however, if the layers demonstrate appropriate durability and integrity, a support is not needed.

In one preferred embodiment, an integral analytical element of this invention comprises a radiation-transmissive support having thereon, (1) a reagent layer that is permeable to at least bilirubin and which contains an interactive mordant composition for bilirubin as described above, and (2) a spreading layer that is permeable to bilirubin. The reagent layer is interposed between the support and the spreading layer. Also, the spreading layer is preferably of substantially uniform permeability to bilirubin. Preferably, the reagent layer is substantially impermeable to protein materials having a molecular weight substantially greater than that of bilirubin, e.g., albumin and other protein materials having a molecular weight in the region of 60,000 (dalton units) or higher.

In accordance with a further aspect of the present invention, there is provided an integral analytical element with a support having thereon a reagent layer and a spreading layer, all as described above with respect to the foregoing preferred embodiment. Additionally, however, there is included in elements according to this preferred embodiment a non-fibrous spreading layer, desirably isotropically porous. In one aspect of this embodiment, all layers are preferably non-fibrous, to enhance quantitative analytical capability of the element. The term "non-fibrous" is used herein with respect to layers and/or materials to indicate that such layers or materials are free or substantially free from fibrous materials, that is, they do not include fibrous components to a degree that would interfere with sample spreading as discussed herein or with detection of the analytical result by radiometric means.

When used in association with a spreading layer, reagent layers in the elements of this invention are desirably uniformly permeable to bilirubin but substantially impermeable and nonporous to higher molecular weight protein materials. As used herein the term permeability includes permeability arising from porosity, ability to swell or any other characteristic. Reagent layers can include a matrix in which the interactive mordant composition is distributed, i.e., dissolved or dispersed. However, as is often the case in the present invention where the interactive mordant composition is polymeric and is itself film-forming or otherwise readily coatable as a uniform layer or zone, such an additional matrix material is not required. The choice of a matrix material is, of course, variable and dependent on the components of the interactive mordant composition distributed therein. In any case, the matrix material should be "non-interfering" with respect to the mordant composition, i.e., the matrix material should be incapable of itself binding or mordanting to the interactive mordant composition. Desirable matrix materials for reagent layers associated with spreading layers are non-fibrous and can include non-interfering hydrophilic materials including acid hydrolyzed gelatins (e.g. pig gel) and derivatives thereof having an isoelectric point of about 9.1, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Non-interfering organophilic materials such as cellulose esters and the like can also be useful. To enhance permeability of the reagent layer, if not porous, it is often useful to use a matrix material that is swellable in the solvent or dispersion medium of liquid under analysis. Also, it may be necessary to select a material that is compatible with the application of an adjacent layer, such as by coating means, during manufacture of the element. As an example, where the formation of discrete, contiguous layers is desired and the intended analysis will be of aqueous liquids, it may be appropriate to select an essentially water soluble matrix for the reagent layer and essentially organosoluble or organo dispersible ingredients for an adjacent layer, such as a spreading layer. In such manner, mutual solvent action is minimized and a clearly delineated layer structure can be formed. In many cases, to prevent diffusion of high molecular weight protein materials into the reagent layer (which materials may be potential bilirubin interferents), it may be desirable to have the reagent layer of lower permeability than is the spreading layer itself. This can readily be accomplished by reducing the effective pore size of the reagent layer. Relative permeability or porosity can be determined by well-known techniques.

Within the reagent layer is distributed an interactive mordant composition for bilirubin. The distribution of interactive composition can be obtained by dissolving or dispersing it in a matrix material, if used. Although uniform distributions are often preferred, they may not be necessary.

As is the case for a "wet chemistry" or solution assay using an interactive mordant composition for bilirubin as described herein, one can also include in a "dry chemistry" analytical element of the invention an appropriate pH buffering composition. The buffering composition can be incorporated in the reagent layer or in one or more of the other layers present in a particular analytical element of the invention in an amount effective to impart to the reagent layer, under conditions of use of the element, a pH essentially identical to that employed in a solution assay. Various buffering compositions can be used including phosphate buffers and others such as those described by Good in *Biochemistry* 5, 467 (1966).

As mentioned previously, an integral element of this invention typically includes a spreading layer. The spreading layer is a layer that can accept a liquid sample, whether applied directly to the spreading layer or provided to it from a layer or layers in fluid contact with the spreading layer, and within which the solvent or dispersion medium of the sample and bilirubin is distributed such that a uniform apparent concentration of bilirubin is provided at the surface of the spreading layer facing the reagent layer of the element. It will be appreciated that such an apparent concentration can be achieved with concentration gradients present through the thickness of or otherwise in the spreading layer. Such gradients do not present any difficulty to obtaining quantitative test results and can be accommodated using known calibration techniques.

The mechanism of spreading is not fully understood, but it is believed that spreading results from and is limited by a combination of forces such as hydrostatic pressure of a liquid sample, capillary action within the spreading layer, surface tension of the sample, wicking action of layers in fluid contact with the spreading layer, and the like. As will be appreciated, the extent of spreading is dependent in part on the volume of liquid to be spread. However, it should be emphasized that the uniform apparent concentration obtained with spreading is substantially independent of liquid sample volume and will occur with varying degrees of spreading. As a result, elements of this invention do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g. one square centimeter), there is no need to remove excess moisture from the element after application of a liquid sample. Further, because spreading occurs in the spreading layer and the spread substance is provided to the fluid contacting reagent layer and without apparent substantial lateral hydrostatic pressure, there is not the "ringing" problem often seen with prior analytical elements.

The spreading layer need only produce a uniform apparent concentration of spread substance per unit area at its surface facing a reagent layer with which the spreading layer is in fluid contact, and it is very convenient to determine whether a particular layer can be suitable for spreading purposes. Such uniformity of apparent concentration can be determined by densitometric or other analytical techniques and, if desired, a specific test for this property is set forth in detail in the aforementioned U.S. Pat. No. 3,992,158.

Useful spreading layers are desirably isotropically porous layers. Reference herein to isotropic porosity identifies the fact of porosity in all direction within the spreading layer. It will be understood that the degree of such porosity may be variable, if necessary or desirable, for example, regarding pore size, percentage of void volume or otherwise. Further information as to the term isotropic porosity (or isotropically porous) as used herein may be found, if desired, in the aforementioned U.S. Pat. No. 3,992,158.

Useful spreading layers can be prepared using a variety of components as more fully described in the aforementioned U.S. Pat. No. 3,992,158. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers, e.g. microcrystalline cellulose. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer.

As an alternative or in addition to such particulate materials, the spreading layer can be prepared using isotropically porous polymer compositions. It is possible to prepare such polymer compositions using techniques useful in forming blushed polymers, for example, as described in U.S. Pat. No. 3,555,129 and in the aforementioned U.S. Pat. No. 3,992,158. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575. Many different polymers can be used, singly or in combination, for preparing isotropically porous blushed polymer spreading layers for use in this invention, typical examples being polycarbonates, polyamides, polyurethanes and cellulose esters such as cellulose acetate. Various microporous filters are or are partly blushed polymeric compositions, for example, various membrane filters or Millipore Corporation, and they have been described in patents such as U.S. Pat. No. 2,783,894 and U.S. Pat. No. 2,772,322.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous blushed polymers are used in the spreading layer. Further information regarding void volume of the spreading layer as well as methods of calculating void volume are set forth in U.S. Pat. No. 3,992,158.

In preparing integral analytical elements of this invention, the layers can be performed as separate layers which can thereafter be laminated prior to use or maintained as separate layers until brought into fluid contact when the element is in use. Layers preformed as separate members, if coatable, are typically coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on those coated previously. Such coating can be accomplished by various well-known coating techniques as described in further detail in the aforementioned U.S. Pat. No. 3,992,158. Any interlayer adhesion problems can be overcome without harmful effect by means of surface treatments including extremely thin application of subbing materials such as are used in photographic films.

For coatable reagent layers, a coating solution or dispersion including the matrix material, if one is used, and interactive mordant compositions can be prepared, coated as discussed herein and dried to form a dimensionally stable layer. The thickness of any reagent layer and its degree of permeability are widely variable and depend on actual usage. Dry thickness of from about 10 microns to about 100 microns have been convenient, although more widely varying thicknesses may be preferable in certain circumstances. Fibrous reagent layers can be formed by impregnation of a fibrous matrix, in accordance with well-known techniques.

As mentioned previously herein, the present analytical elements can be self-supporting or carried on a support. Useful support materials include a variety of polymeric materials such as cellulose acetate, poly(ethylene terephthalate), polycarbonates and polyvinyl compounds such as polystyrenes, etc. A support of choice for any particular element will be compatible with the intended mode of result detection. Preferred supports include radiation-transmissive support materials that transmit electromagnetic radiation of a wavelength or wavelengths within the region between about 300 nm and about 700 nm. It may also be desirable to have a support that transmits one or more narrow wavelenth bands and is opaque to adjacent wavelength bands. This could be accomplished, for example, by impregnating or coating the support with one or more colorants having suitable absorption characteristics.

The components of any particular layer of an element of this invention, and the layer configuration of choice, can vary considerably. As stated previously, spreading layer pore size can be chosen so that the layer can filter out undesirable sample components such as proteins having a higher molecular weight than bilirubin and that would, for example, interfere with the analytical displacement reaction or with the detection of any test result produced within the element. For analysis of whole blood, porous layers having a pore size of from 1 to about 5 microns are particularly useful in screening out blood cells, which typically have a size of from 7 to about 30 microns. If desirable, an element can include a plurality of spreading layers, each of which may be different in its ability to spread and filter.

In the layers of the element, it can be advantageous to incorporate one or more surfactant materials such as anionic and nonionic surfactant materials. They can, for example, enhance coatability of layer formulations and enhance the extent and rate of spreading in spreading layers that are not easily wetted by liquid samples in the absence of an aid such as a surfactant. In particular, it can be desirable to incorporate a relatively large amount of a surfactant, such as a non-ionic surfactant, in the spreading layer of the elements of the invention to normalize transport of bilirubin contained in an aqueous proteinaceous liquid sample in and through this layer of the element. Such normalization refers to obtaining within the spreading layer an equivalent penetration of the solvent medium and bilirubin contained in various applied samples of aqueous proteinaceous liquids, notwithstanding variations in protein concentration between such samples. In addition, it has been found that in the total bilirubin assay of the invention wherein bilirubin is often present in a "bound-state" such as bound to other proteins, e.g., serum albumin, the use of such surfactants in the spreading layer to achieve normalization of bilirubin transport advantageously appears to dissociate bilirubin bound to such protein. Preferred amounts of surfactant effective to achieve normalized bilirubin transport are typically between about 1% and about 15% by weight based on the dry weight of the layer. Further details regarding this use of surfactant materials to achieve normalized analyte transport may be found by reference to Goffe et. al., copending U.S. patent application Ser. No. 680,619, filed Apr. 26, 1976.

Analytical elements of the present invention can be adapted for use not only in the field of clinical chemistry, but in chemical research and in chemical process control laboratories. They are well suited for use in clinical testing of body fluids, such as blood, blood serum and urine, such in this work a large number of repetitive tests are frequently conducted and test results are often needed a very short time after the sample is taken. In analyzing blood with the analytical element of this invention, the blood cells may first be separated from the serum, by such means as centrifuging, and the serum applied to the element. However, it is not necessary to make such separation, for example, if reflective spectrophotometric analysis techniques are used to quantify or otherwise analyze for the mordanted bilirubin. Whole blood can be applied directly to the element and the blood cells filtered out and excluded from the reagent layer through the action of a separate interlayer serving as a filtering layer, which can also be a radiation-blocking layer. The presence of these cells on the element will not interfere with spectrophotometric analysis if it is carried out by reflection techniques, with light being transmitted through the support and registration layer and reflected from the radiation-blocking layer or other reflecting layer such that detecting radiation does not intercept the cells. A particularly significant advantage of the integral analytical elements described herein is their ability to be used to analyze either serum or whole blood.

As mentioned previously, elements of this invention can include a radiation-blocking layer, preferably interposed between a reagent layer and the support. Radiation-blocking layers serve to inhibit passage of electromagnetic radiation, such as at the wavelength or wavelengths used for detection. Such layers include an opacifying agent that, by virtue of its absorbance, reflectance or the like, provides a radiation inhibiting effect when incorporated into the layer. In one aspect, the radiation-blocking layer can include a matrix containing an opacifying agent, such as a pigment like carbon or other inorganic pigment such as a metal salt like titanium dioxide, zinc oxide, barium sulfate, etc. Blushed polymers, which are generally reflective in nature, can comprise the opacifying agent and layers of such blushed polymers as are useful in spreading layers can be used also as radiation-blocking layers.

In one preferred aspect, blushed polymer spreading layers can also incorporate a reflective inorganic pigment, such as the highly reflective pigments mentioned elsewhere herein, to enhance spreading and/or reflectivity. The amount of pigment that can be included in a layer together with blushed polymer is highly variable, and amounts of from about 5 percent by weight to about 1,000 percent by weight of pigment based on the weight of blushed polymer are preferred, with a pigment concentration of from about 100 weight percent to about 600 weight percent based on the blushed polymer being most preferred.

In addition to the use of an optional radiation-blocking layer in an integral analytical element of the invention, other optional interlayers may also be incorporated, if desired. For instance, a separate interlayer swellable in the solvent or disperion medium of the liquid sample under analysis can be used. Such a swellable interlayer, preferably radiation-transmissive, e.g., a swellable gel layer, can be incorporated between the reagent layer and support of an integral analytical element and could be used to enhance the permeation or "spread rate" of a bilirubin-containing serum sample through the spreading layer into the reagent layer of the element. As another example an interlayer can be incorporated into an analytical element of the invention between the spreading layer and the reagent layer thereof. Such a layer should, of course, be permeable to bilirubin and can be used to incorporate reagent materials that can render various interferents for bilirubin inactive or can be used to filter and thereby remove such interferent materials. Or, in a further variation, such an interlayer can be used to incorporate a reagent that can be used to react with bilirubin. For example, a gel interlayer containing the enzyme glucuronidase can be employed between the spreading layer and the layer containing the interactive mordant composition whereby the enzymatic action of glucuronidase is used to convert conjugated bilirubin in the liquid sample under analysis into the unconjugated form of bilirubin. Alternatively, the enzyme glucuronidase may be incorporated in the spreading layer of an analytical element of the invention for more direct and efficient interaction of the enzyme on the incoming conjugated form of bilirubin.

As can be appreciated, a variety of different elements can be prepared in accordance with the present invention. Elements can be configured in a variety of forms, including elongated tapes of any desired width, sheets or smaller chips.

The preferred integral elements are placed in use by applying to the element a sample of liquid under analysis. Typically, an element will be formed such that an applied sample will contact a spreading layer prior to the reagent layer and will first contact such spreading layer at its surface furthest removed from such reagent layer. Because analytical accuracy of the present elements is not substantially diminished by variations in the volume of applied samples, sample application by hand or machine is acceptable. For reasons of convenience in detecting an analytical result, however, reasonable consistency in sample volume may be desirable. As discussed previously, the spreading layer is also extremely desirable in minimizing the occurrence of ringing when soluble interactive compositions are used in a reagent layer.

In a typical analytical procedure using the present integral elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, the element is exposed to any conditioning, such as heating, humidification, or the like, that may be desirable to quicken or otherwise facilitate obtaining any test result. If an automated procedure is used, it can also be desirable to have any spreading layer accomplish its function within several seconds, but allowing sufficient time to provide metering, which is contrasted with the almost instantaneous, unregulated diffusion as can be obtained with absorbent fibrous papers. This can be accomplished conveniently by appropriate selection of various parameters, such as layer thickness, void volume in porous layers, etc.

After the analytical result is obtained as a detectable change, it is measured, usually by passing the element through a zone in which suitable apparatus for reflection or transmission spectrophotometry is provided. Such apparatus would serve to direct a beam of energy, such as light, through the support and the reagent layer. The light would then be reflected, such as from an opacifying agent in the spreading or a radiation-blocking layer in the element, back to a detecting means or would pass through the element to a detector, in the case of transmission detection. In a preferred mode, the analytical result is detected in a region of the element totally within the region in which such result is produced. Generally, electromagnetic radiation in the range of from about 300 to about 700 nm has been found useful for such measurements, although any radiation to which the element is permeable and which is capable of quantifying the detectable change produced in the reagent layer can be used. Various calibration techniques can be used to provide a control for the analysis. As one example, a sample of analyte standard solution can be applied adjacent to the area where the drop of sample is placed in order to permit the use of differential measurements in the analysis.

The following examples are presented to further illustrate the present invention.

EXAMPLE 1

Solution Assay for Bilirubin

In this example, it was demonstrated that bilirubin, in a liquid assay medium and in the presence of certain mordants, specified hereinabove, shifts its $\lambda_{max}$ (maximum absorption peak) from 435–440 nm. to 460 nm., with a marked enhancement of its molar extinction at this new absorption peak. To demonstrate this, the absorption spectra (360–600 nm., read on a spectrophotometer at 37° C) were recorded from four liquid solution samples identified as A through D below:

A. 0.05 M sodium dihydrogen phosphate buffer, pH 7.4
B. 0.012% (w/v) Mordant 6 of Table I in sodium dihydrogen phosphate buffer, pH 7.4
C. 1. mg./dl. bilirubin in sodium dihydrogen phosphate buffer, pH 7.4
D. 1 mg./dl, bilirubin + 0.012% (w/v) of Mordant 6 of Table I in sodium dihydrogen phosphate buffer, pH 7.4

The absorption spectra results obtained illustrated that 1. at the levels tested, neither the phosphate buffer (solution A) nor Mordant 6 alone (solution B) contribute significantly to the absorption anywhere over this spectral range;
2. bilirubin alone (solution C) has an absorption maximum ($\lambda_{max}$) at 435 –440 nm.; and
3. bilirubin in the presence of Mordant 6 of Table I (solution D) results in a shift in its $\lambda_{max}$ to 460 nm., accompanied by a two-fold increase in its absorption at the new peak, i.e., $$E_{m460} \, 40 \times 10^3 \rightarrow E'_{m460} \, 80 \times 10^3$$

($E_{m460}$ represents molar extinction coefficient of bilirubin alone)
($E'_{m460}$ represents molar extinction coefficient of bilirubin and Mordant 6 of Table I)

EXAMPLE 2

Application of Bilirubin-Mordant Interaction in an Analytical Element

In a preferred embodiment of the present invention, an integral analytical element structure was prepared as follows:

A transparent polyethylene terephthalate web support was coated with a reagent layer consisting solely of mordant 4 to Table I (0.54 g/m²); a subbing layer containing poly(n-isopropyl acrylamide) (0.32 g/m²) and a blushed polymer spreading layer containing $TiO_2$ (45.6 g/m²), cellulose acetate 6.45 g/m²), Triton X-405 ®, i.e., octyl phenoxy polyethoxy ethanol sold by Rohm & Haas Co., (2.51 g/m²) and oleic ether of polyethylene glycol (0.64 g/m²).

Figure 3:
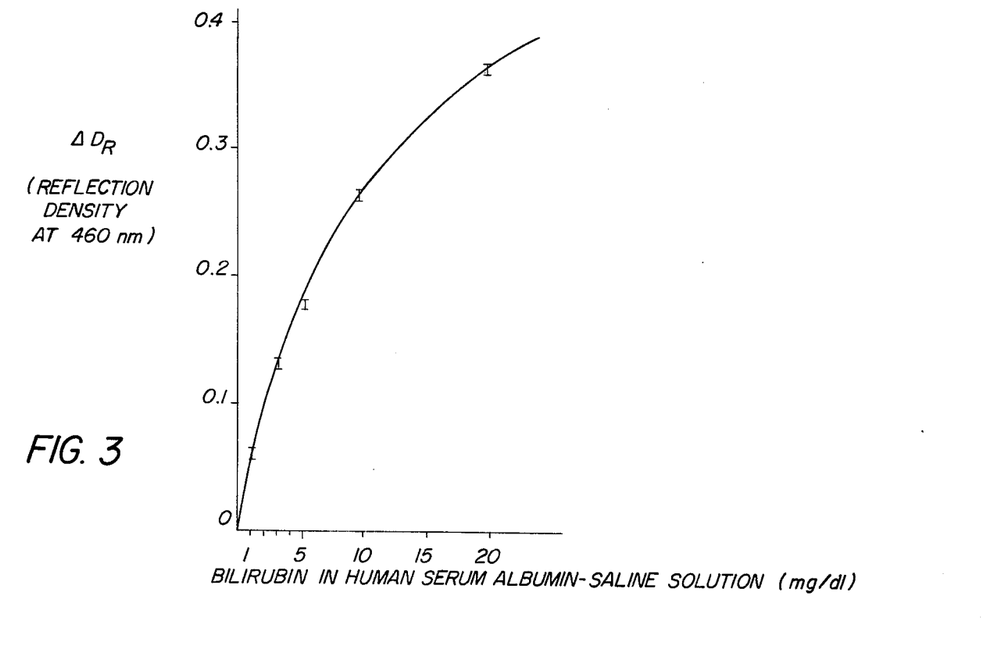
FIG. 3 is a graph illustrating the spectrophotometric response of a preferred multilayer analytical element of the invention to varying levels of bilirubin concentration.

The element was then evaluated in the following manner:

A series of bilirubin solutions containing 7 g./dl. human serum albumin and 100 mM saline and amounts of bilirubin varying from 0 to 20 mg. bilirubin per deciliter of solution were spotted (using ~ 10 microliter drops) to the coated element. The change in reflection density, $\Delta D_R$, of the analytical element of this example (as measured at 460 nm. and at 37° C.) were recorded at 7 minutes. FIG. 3 shows the response of this element over the 0–20 mg/dl. bilirubin range tested.

Excellent reproducbility, as shown by the vertical bars at each point on the curve, was obtained from this element.

EXAMPLE 3

Application of Bilirubin-Mordant Interaction in an Analytical Element Using Mordant and Gelatin In another embodiment of the present invention, a web structure was prepared as follows:

A transparent polyethylene terephthalate web support was coated with a reagent layer containing Mordant 6 of Table I (2.2 g/m$^2$) and gelatin (4.1 g/m$^2$) and a spreading layer identical to that used in Example 2.

The web was then evaluated as described in Example 2. A series of aqueous solutions containing varying amounts of bilirubin and having a pH of 7.4 and a series of saline solutions having a pH of 7.4 and containing 7 g./dl. albumin and varying amounts of bilirubin were used as liquid test samples. As a result it was found that the element of this example exhibited a highly linear spectrophotometric response to a wide range of differing bilirubin concentrations. Also, the insensitivity of this element to albumin was demonstrated by the good agreement obtained from the element of this example regardless of whether or not the liquid test sample contained albumin.

EXAMPLE 4

Application of Bilirubin-Mordant Interaction in an Analytical Elment Using a Gel Pad In a further embodiment of the present invention, an analytical element structure was prepared as follows:

The support used in Example 2 was coated with a gel pad containing bovine serum albumin (1.1 g/m$^2$) and gelatin (2.3 g/m$^2$); a reagent layer containing Mordant 6 of Table I (1.1 g/m$^2$) and gelatin (1.1 g/m$^2$); and a spreading layer as described in Example 2.

The web was then evaluated in a manner similar to that described in Example 2. Aqueous solutions (obtained from American Monitor Corp., Indianapolis, Ind. which contained 7g./dl. human serum albumin in saline and varying levels of bilirubin were used as a calibrator for the element. Then the calibrated element was used to test several commercially-available human serum surrogates of diverse compositions having a known bilirubin content. Bilirubin values measured by the element of this example (over a bilirubin concentration range of 0.5 to 20.0 mg/dl) agreed very well with those specified by the human serum surrogate manufacturers.

EXAMPLE 5

Lack of Spectral Interference due to Hemoglobin

Most, if not all, other direct spectrophotometric assays of bilirubin suffer from spectral interference due to hemoglobin which is present in serum in amounts less than 20 mg/dl. To demonstrate that the multilayer analytical elements of the present invention are substantially free of spectral interference due to hemoglobin, identical elements of the invention prepared as in Example 3 were spotted with liquid test samples containing either 1 mg./dl. or 15 mg./dl. of bilirubin and varying amounts of hemoglobin ranging from 0 to 150 mg/dl., and the reflection density, $D_R$, at 460 nm. of each element was measured. No change in the response of the elements was observed over this wide range of hemoglobin concentration, thereby indicating that hemoglobin was not an interferent in this assay at 460 nm.

EXAMPLE 6

Effect of pH variations

To demonstrate the insensitivity of this bilirubin assay to pH variations which may occur in samples such as blood sera, two series of bilirubin standards (having a bilirubin concentration varying over the range of 0–20 mg/dl), one at pH 7.4 and the other at pH 8.2, containing 7 g./dl. human serum albumin, saline and 0.05 N sodium dihydrogen phosphate buffer, were spotted onto analytical elements prepared as in Example 2. The elements were evaluated in a manner similar to that described in Example 2. Results indicated no sensitivity to pH variations in the range tested.

EXAMPLE 7

Effect of Temperature Variation

Analytical elements prepared as described in Example 3 were used to test the sensitivity of the elements to temperature variations. A series of bilirubin standards at pH 7.4 was used. Although element response was noticeably lower at 27° C, it was virtually invariant between 37° C and 42° C.

EXAMPLE 8

Keeping Properties

Analytical elements and a series of bilirubin standards as described above in Example 7 were used to test the stability of the elements over a one-month period at room temperature (20° C). As a result, it was found that the elements appeared to be extremely stable at room temperature over this period of time, without special humidity controls. Not only did the element remain calibratable, but the response of the aged element was essentially indistinguishable from that of the fresh.

EXAMPLE 9

Lack of Carotenoid Interference

β-carotene, the principal carotenoid in adult serum, has been cited as a potential interferent in direct spectrophotometric assays for bilirubin because it absorbs at 450 nm. In this example, the spectrophotometric responses of an analytical element of the present invention (prepared as described in Example 2) to four saline liquid test solutions containing 7 g./dl. albumin, 1 or 20 mg/dl. bilirubin, and 0.02 or 0.2 mg/dl. β-carotene were recorded. The presence of β-carotene at these levels, which span its normal range in human serum, was found to have no demonstrable effect on the element.

The invention has been described in detail with particular reference to certain preferred embodiments thereof, but it will be understood that variations and modifications can be effected within the spirit and scope of the invention.

We claim:
1. A colorimetric method for the detection of bilirubin in an aqueous liquid which comprises
    a. contacting in a reagent zone said aqueous liquid and an interactive mordant composition for bilirubin, such interactive mordant composition having one or more binding sites for bilirubin and comprising a hydrophobic organic matrix and at least one charge-bearing cationic group,
   whereby bilirubin is mordanted, said mordanted bilirubin exhibiting an absorption peak shifted at least about

10 nm. from that of free bilirubin and a molar extinction coefficient at least about 50 percent higher than that of free bilirubin, and b. colorimetrically detecting said mordanted bilirubin.

2. The method of claim 1 wherein said interactive mordant composition is admixed in a non-interfering liquid medium and is contacted with said aqueous liquid in a reaction zone at a pH of from about 6.8 to about 9.5 and at a temperature of from about 15° to about 60° C.

3. The method of claim 1 wherein said aqueous liquid containing bilirubin is a biological liquid.

4. The method of claim 1 wherein said aqueous liquid containing bilirubin is blood serum.

5. The method of claim 1 wherein said aqueous liquid containing bilirubin is blood serum which has been pretreated to reduce the amount of protein contained therein.

6. The method of claim 1 wherein said interactive mordant composition for bilirubin is a polymeric material having repeating units of the following formula wherein A represents an organo group, Q represents a chemical bond(s) or a chemical group linking M+ to A, M+ represents a quaternary ammonium or phosphonium group, and X− represents an acid anion.

7. The method of claim 1 wherein said interactive mordant composition for bilirubin is a polymeric material having repeating units of the following formula:

wherein A represents an alkylene group, Q represents a hydrocarbon group linking the nitrogen atom to A and contains from about 5 to about 10 carbon atoms, each of $R^1$, $R^2$, and $R^3$, which may be the same or different, represents an alkyl having from 1 to less than about 10 carbon atoms or an aryl, aralkyl or alkaryl having from 5 to less than about 20 carbon atoms, and X represents an acid anion.

8. The method of claim 1 wherein said interactive mordant composition for bilirubin is a polymeric material representing a copolymerized blend of monomers comprising (a) from about 25 to about 90 weight percent of monomer precursors for repeating units having the formula wherein A represents an alkylene group, Q represents a hydrocarbon group linking the nitrogen atom to A and contains from about 5 to about 10 carbon atoms, each of $R^1$, $R^2$, and $R^3$, which may be the same or different, represents an alkyl having from 1 to less than about 10 carbon atoms or an aryl, aralkyl or alkaryl having from 5 to less than about 20 carbon atoms, and X represents an acid anion, (b) from about 10 to about 75 weight percent of monomer precursors for non-interfering repeating monomeric units, said monomer precursors selected from the group consisting of aliphatic and aromatic hydrocarbons, alkyl acrylates, and alkyl methacrylates, and (c) from 0 to about 5 weight percent of a difunctional crosslinking agent.

9. The method of claim 1 wherein said interactive mordant composition is a material selected from the group consisting of poly(N,N,N-trimethyl-N-vinyl-benzylammonium) chloride; poly[styrene-co-benzyl(dimethyl)-p-vinyl-benzylammonium chloride]; poly[styrene-co-vinylbenzyl-N,N-dimethylbenzyl-ammonium chloride-co-divinylbenzene]; poly(N,N,N-trimethyl-N-vinylbenzylammonium chloride-co-styrene); poly(N,N,N-trioctyl-N-vinylbenzylphosphonium chloride; and poly(styrene-co-(vinylbenzyl)-(tridexyl)-ammonium chloride).

10. An element for the colorimetric detection of bilirubin in an aqueous liquid, said element having a spreading zone and a reagent zone in fluid contact under conditions of use, said element free from any reagent zone which contains highly colored dyestuff or fluorescent probe materials or precursors for such materials, said reagent zone comprising an interactive mordant composition for bilirubin, such interactive mordant composition a. having one or more binding sites for bilirubin and comprising a hydrophobic organic matrix and at least one charge-bearing cationic group, and b. upon mordanting bilirubin, exhibiting an absorption peak shifted at least about 10 nm. from that of free bilirubin and a molar extinction coefficient at least about 50 percent higher than that of free bilirubin.

11. An element in accord with claim 10 wherein said spreading zone and reagent zone are superposed layers carried on a radiation transmissive support, said reagent layer interposed between the support and the spreading layer.

12. An element in accord with claim 10 wherein said interactive mordant composition is a polymeric material having repeating units of the following formula:

wherein A represents an organo group, Q represents a chemical bond(s) or a chemical group linking M+ to A, M+ represents a quaternary ammonium or phosphonium group, and X− represents an acid anion.

13. An element in accord with claim 10 wherein said spreading zone and reagent zone are superposed layers carried on a radiation transmissive support, said reagent layer interposed between the support and the spreading layer, said spreading layer containing an amount of surfactant effective to normalize transport of bilirubin through said layer.

14. An integral element for the detection of bilirubin in an aqueous liquid, said element comprising a spreading layer superposed over a reagent layer carried on a radiation transmissive support, said element free from any reagent layer which contains a highly colored dyestuff or fluorescent probe material or precursors for such materials, said spreading layer and reagent layer in fluid contact under conditions of use, said spreading layer comprising an isotropically porous, non-fibrous composition containing an amount of surfactant effective to normalize transport of bilirubin through said layer, said reagent layer comprising an interactive mordant composition for bilirubin, such interactive composition a. upon mordanting bilirubin, exhibiting an absorption peak shifted at least about 10 nm. from that of free bilirubin and a molar extinction coefficient at least about 50 percent higher than that of free bilirubin, and b. comprising a polymeric material having repeating units of the following formula:

wherein A represents an alkylene group, Q represents a hydrocarbon having a group linking the nitrogen atom to A and containing from about 5 to about 10 carbon atoms, each of $R^1$, $R^2$, and $R^3$, which may be the same or different, represents an alkyl having from 1 to less than about 10 carbon atoms or an aryl, aralkyl or alkaryl having from 5 to less than about 20 carbon atoms, and $X^-$ represents an acid anion.

15. An element according to claim 14 wherein said interactive mordant composition for bilirubin comprises a polymeric material representing a copolymerized blend of momomers comprising (a) from about 25 to about 90 weight percent of monomer precursors for repeating units having the formula wherein A represents an alkylene group, Q represents a hydrocarbon having a group linking the nitrogen atom to A and containing from about 5 to about 10 carbon atoms, each of $R^1$, $R^2$, and $R^3$, which may be the same or different, represents an alkyl having from 1 to less than about 10 carbon atoms or an aryl, aralkyl or alkaryl having from 5 to less than about 20 carbon atoms, and $X^-$ represents an acid anion, (b) from about 10 to about 75 weight percent of monomer precursors for non-interfering repeating monomeric units, selected from the group consisting of aliphatic and aromatic hydrocarbons, alkyl acrylates, and alkyl methacrylates, and (c) from 0 to about 5 weight percent of a difunctional crosslinking agent.

16. An element according to claim 14 wherein said element comprises a water swellable interlayer between said reagent layer and said support.

17. An element according to claim 14 wherein said element comprises an interlayer containing glucuronidase between said spreading layer and said reagent layer.

18. An element according to claim 14 wherein said element contains glucuronidase in the spreading layer thereof.

19. An element according to claim 14 wherein said spreading layer comprises a porous polymeric composition or particulate matter.

20. An element according to claim 14 wherein said spreading layer comprises particulate material dispersed in a polymeric composition.

21. An element according to claim 14 wherein said interactive mordant composition comprises a polymeric material selected from the group consisting of poly(N,N,N-trimethyl-N-vinyl-benzylammonium) chloride; poly[styrene-co-benzyl(dimethyl)-p-vinyl-benzylammonium chloride]; poly[styrene-co(vinylbenzyl)-(trihexyl)-ammonium chloride; poly[styrene-co-N-vinylbenzyl-N,N-dimethylbenzyl-ammonium chloride-co-divinylbenzene]; poly(N,N,N-trimethyl-N-vinylbenzylammonium chloride-co-styrene); and poly(N,N,N-trioctyl-N-vinylbenzylphosphorium chloride).

22. An element according to claim 14 wherein said reagent layer is substantially impermeable to materials having a molecular weight equal to or greater than that of albumin.

23. An element according to claim 14 wherein the reagent layer has a substantially lower permeability than the spreading layer.

* * * * *

UNITED STATES PATENT AND TRADEMARK OFFICE
CERTIFICATE OF CORRECTION

PATENT NO. : 4,069,017
DATED : January 17, 1978
INVENTOR(S) : Tai-Wing Wu and Marshall Dappen It is certified that error appears in the above-identified patent and that said Letters Patent are hereby corrected as shown below:

Column 1, line 22, "is released" should read --are released--.

Column 2, line 35, "absorbtivity" should read --absorptivity--.

Column 2, line 37, "absorbtivity" should read --absorptivity--.

Column 2, line 39, "absorbitivity" should read --absorptivity--.

Column 2, line 44, "Pryzbylowicz" should read --Przybylowicz--.

Column 2, line 50, "receiving" should read --reviewing--.

Column 5, line 60, after "7.4", --.-- should be inserted.

Column 6, line 57, "describe" should read --describes--.

Column 7, line 34, after "properties", "," should be deleted.

Column 8, line 20, "and" should read --or--.

Column 8, line 46, "a" should read --A--.

Columns 11-12, Table I, formula 4, that part of the formula reading:

$$\underset{\overset{|}{C_6 \overset{\oplus}{H}_{13}}}{N} \quad \text{should read} \quad \underset{\overset{|}{C_6 H_{13}}}{\overset{\oplus}{N}}$$

UNITED STATES PATENT AND TRADEMARK OFFICE
CERTIFICATE OF CORRECTION

PATENT NO. : 4,069,017
DATED : January 17, 1978
INVENTOR(S) : Tai-Wing Wu and Marshall Dappen It is certified that error appears in the above-identified patent and that said Letters Patent are hereby corrected as shown below:

Columns 11-12, Table I, formula 5, that part of the formula reading:

$$\begin{array}{c} N \\ | \\ CH_3^{\oplus} \end{array} \qquad \text{should read} \qquad \begin{array}{c} N_{,\oplus} \\ | \\ CH_3 \end{array}$$

Columns 11-12, Table I, polymer No. 6, "Poly(styrene-co-N-vinylbenzyl-N,N-dimethylbenzylammonium chloride-co-divinyl-benzene)" should read -- Poly(styrene-co-N-vinyl-benzyl-N-benzyl-N,N-dimethylammonium chloride-co-divinyl-benzene) --.

Column 13, line 41, "causes" should read --cause--.

Column 13, line 62, "affecting" should read --effecting--.

Column 17, line 3, "direction" should read --directions--.

Column 17, line 52, "filters or" should read --filters of--.

Column 18, line 14, "performed" should read --preformed--.

Column 18, line 39, "thickness" should read --thicknesses--.

Column 18, line 57, "wavelenth" should read --wavelength--.

Column 22, line 50, before "6,45", --(-- should be inserted.

Column 22, line 61, "to" should read --onto--.

Column 22, line 63, "were" should read --was--.

UNITED STATES PATENT AND TRADEMARK OFFICE
CERTIFICATE OF CORRECTION

PATENT NO. : 4,069,017
DATED : January 17, 1978
INVENTOR(S) : Tai-Wing Wu and Marshall Dappen It is certified that error appears in the above-identified patent and that said Letters Patent are hereby corrected as shown below:

Column 23, line 28, "Elment" should read --Element--.

Column 23, line 40, after "Ind.", --)-- should be inserted.

Column 24, line 10, "N" should read --M--.

Column 25, line 48, "X" should read --$X^\theta$--.

Column 26, line 2, "X" should read --$X^\theta$--.

Column 26, line 57, "10" should read --11--.

Signed and Sealed this

Twenty-second Day of August 1978

[SEAL]

Attest:

RUTH C. MASON
Attesting Officer

DONALD W. BANNER
Commissioner of Patents and Trademarks